(12) United States Patent
Mossavat et al.

(10) Patent No.: US 9,760,018 B2
(45) Date of Patent: Sep. 12, 2017

(54) METHOD AND INSPECTION APPARATUS AND COMPUTER PROGRAM PRODUCT FOR ASSESSING A QUALITY OF RECONSTRUCTION OF A VALUE OF A PARAMETER OF INTEREST OF A STRUCTURE

(71) Applicant: ASML Netherlands B.V., Veldhoven (NL)

(72) Inventors: Seyed Iman Mossavat, Veldhoven (NL); Hugo Augustinus Joseph Cramer, Veldhoven (NL); Willem Jan Grootjans, Veldhoven (NL); Adriaan Johan Van Leest, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 8 days.

(21) Appl. No.: 14/906,898

(22) PCT Filed: Aug. 5, 2014

(86) PCT No.: PCT/EP2014/066840
§ 371 (c)(1),
(2) Date: Jan. 21, 2016

(87) PCT Pub. No.: WO2015/022239
PCT Pub. Date: Feb. 19, 2015

(65) Prior Publication Data
US 2016/0154319 A1    Jun. 2, 2016

Related U.S. Application Data

(60) Provisional application No. 61/865,354, filed on Aug. 13, 2013.

(51) Int. Cl.
*G01B 11/04*  (2006.01)
*G01N 21/00*  (2006.01)
(Continued)

(52) U.S. Cl.
CPC ....... *G03F 7/705* (2013.01); *G01N 21/95607* (2013.01); *G03F 7/70625* (2013.01); *G03F 9/7092* (2013.01); *G01N 21/956* (2013.01)

(58) Field of Classification Search
CPC .......... G01N 21/956; G01N 21/95607; G01N 21/95615; G03F 7/705; G03F 7/70625;
(Continued)

(56) References Cited

U.S. PATENT DOCUMENTS 6,609,086 B1   8/2003   Bao et al.
7,522,293 B2   4/2009   Wu et al.
(Continued)

FOREIGN PATENT DOCUMENTS

CN   1646661 A   7/2005
CN   1892439 A   1/2007
(Continued)

OTHER PUBLICATIONS

Tollkuhn, B. et al., "Correlation Analysis: A Fast and Reliable Method for Better Understanding of Simulation Models in Optical Lithography", *Proc. of SPIE*, Data Analysis and Modeling for Process Control II, vol. 5755; p. 37-47.
(Continued)

*Primary Examiner* — Colin Kreutzer
(74) *Attorney, Agent, or Firm* — Sterne, Kessler, Goldstein & Fox P.L.L.C.

(57) ABSTRACT

Methods and inspection apparatus and computer program products for assessing a quality of reconstruction of a value of a parameter of interest of a structure, which may be applied for example in metrology of microscopic structures. It is important the reconstruction provides a value of a parameter of interest (e.g. a CD) of the structure which is accurate as the reconstructed value is used to monitor and/or control a lithographic process. This is a way of assessing a
(Continued)

quality of reconstruction (803) of a value of a parameter of interest of a structure which does not require the use of a scanning electron microscope, by predicting (804) values of the parameter of interest of structures using reconstructed values of parameters of structures, and by comparing (805) the predicted values of the parameter of interest and the reconstructed values of the parameter of interest.

19 Claims, 7 Drawing Sheets

(51) Int. Cl.
| | |
|---|---|
| *G03B 27/32* | (2006.01) |
| *G03B 27/74* | (2006.01) |
| *G03F 7/20* | (2006.01) |
| *G01N 21/956* | (2006.01) |
| *G03F 9/00* | (2006.01) |

(58) Field of Classification Search
CPC ... G03F 7/70675; G03F 9/7019; G03F 9/7092
USPC .......................... 355/68, 77; 356/237.5, 636
See application file for complete search history.

(56) References Cited

U.S. PATENT DOCUMENTS

| | | |
|---|---|---|
| 7,523,076 B2 | 4/2009 | Drege et al. |
| 2007/0002336 A1 | 1/2007 | Pellemans et al. |
| 2009/0300573 A1 | 12/2009 | Cao et al. |
| 2012/0123748 A1 | 5/2012 | Aben et al. |
| 2012/0243004 A1 | 9/2012 | El Gawhary et al. |
| 2015/0186557 A1 | 7/2015 | Ye et al. |

FOREIGN PATENT DOCUMENTS

| | | |
|---|---|---|
| CN | 102057329 A | 5/2011 |
| CN | 102209935 A | 10/2011 |
| CN | 102918464 A | 2/2013 |
| EP | 1 628 164 A2 | 2/2006 |
| WO | WO 2011/151121 A1 | 12/2011 |
| WO | WO 2012/138758 A1 | 10/2012 |
| WO | WO 2015/022239 A1 | 2/2015 |

OTHER PUBLICATIONS

Written Opinion of the International Searching Authority with Search Report mailed Nov. 25, 2014, directed to App. No. PCT/EP2014/066840; 11 pages.
International Preliminary Report on Patentability directed to related international patent application No. PCT/EP2014/066840, issued Feb. 16, 2016; 7 pages.

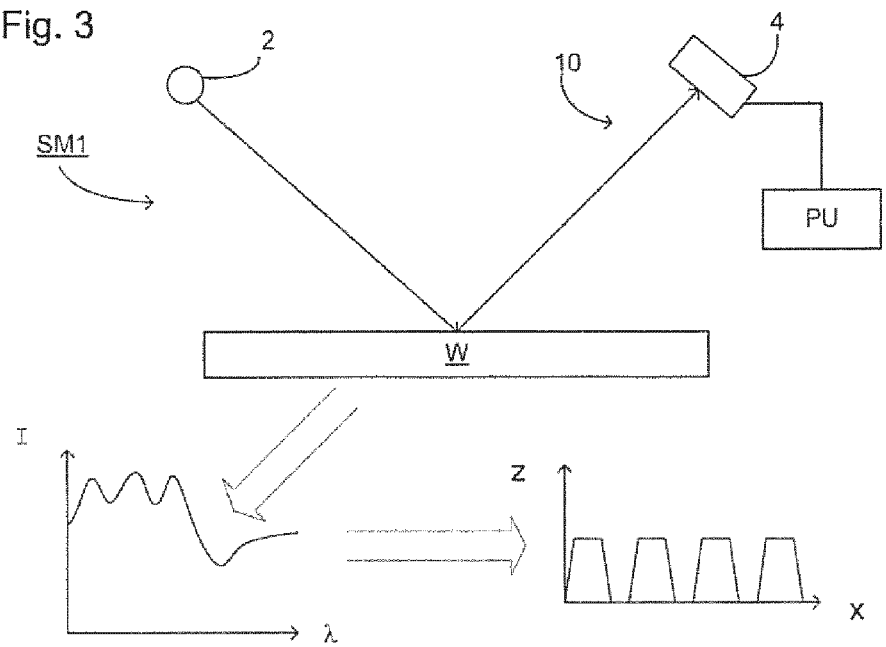
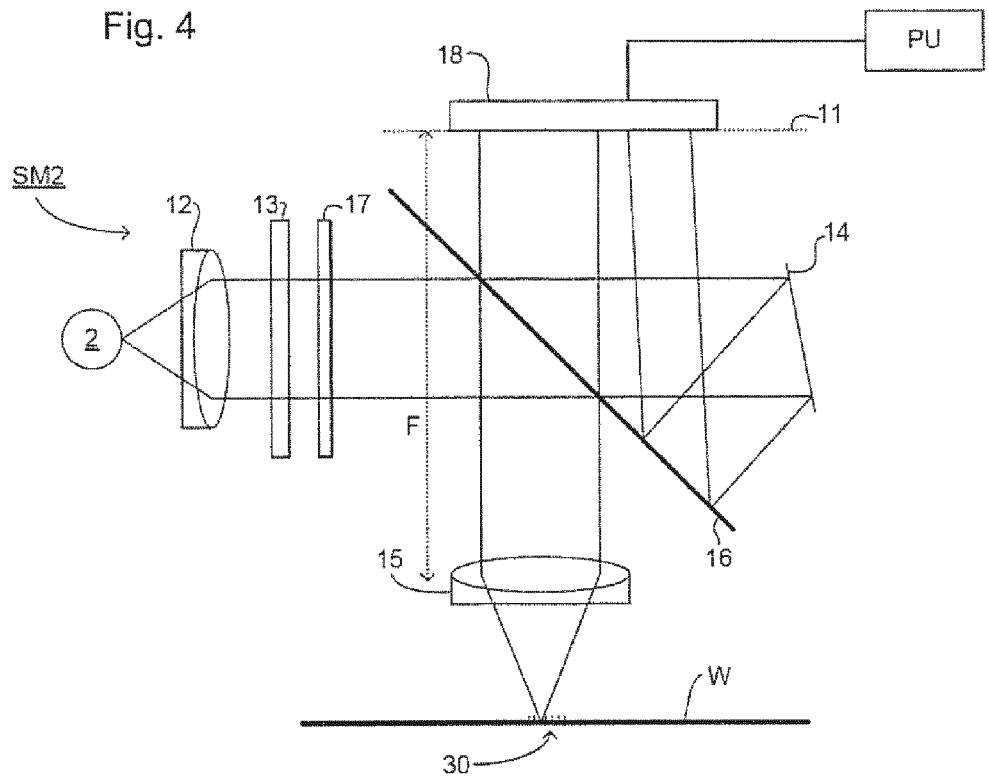

| Ranking | |
|---|---|
| Q | Matching to SEM |
| Recipe 3 | Recipe 3 |
| Recipe 4 | Recipe 4 |
| Recipe 2 | Recipe 2 |
| Recipe 1 | Recipe 1 |
| Recipe 7 | Recipe 10 |
| Recipe 10 | Recipe 7 |
| Recipe 8 | Recipe 6 |
| Recipe 6 | Recipe 5 |
| Recipe 5 | Recipe 8 |
| Recipe 9 | Recipe 9 |

METHOD AND INSPECTION APPARATUS AND COMPUTER PROGRAM PRODUCT FOR ASSESSING A QUALITY OF RECONSTRUCTION OF A VALUE OF A PARAMETER OF INTEREST OF A STRUCTURE

CROSS-REFERENCE TO RELATED APPLICATIONS

This application claims the benefit of U.S. provisional application 61/865,354, which was filed on Aug. 13, 2013 and which is incorporated herein in its entirety by reference.

FIELD

The present invention relates to methods and inspection apparatus and computer program products for assessing a quality of reconstruction of a value of a parameter of interest of a structure. The invention may be applied for example in metrology of microscopic structures, for example to assess critical dimension (CD) performance of a lithographic apparatus.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"—direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth (CD) of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. Two main types of scatterometer are known. Spectroscopic scatterometers direct a broadband radiation beam onto the substrate and measure the spectrum (intensity and/or polarization state as a function of wavelength) of the radiation scattered into a particular narrow angular range. Angularly resolved scatterometers use a monochromatic radiation beam and measure the intensity and/or polarization state of the scattered radiation as a function of angle.

By comparing the properties of the beam before and after it has been reflected or scattered by the substrate, the properties of the substrate, or more specifically one or more properties of one or more structures present on or in the substrate, can be determined. This can be done, for example, by reconstruction by comparing data obtained from measurement of the reflected or scattered beam with model (simulated) diffraction signals calculated from a parameterized (mathematical) model. The calculated signals can be pre-calculated and stored in a library, the library representing a plurality of candidate substrate structures distributed in a parameter space of the parameterized model. Alternatively or in addition, parameters can be varied during an iterative search process, until a calculated diffraction signal matches the measured signal. In U.S. Pat. No. 7,522,293 (Wu), incorporated by reference herein in its entirety, for example, these two techniques are described for example as 'library based' and 'regression based' processes, respectively.

In particular for complex structures, or structures including particular materials, the number of parameters required to model the scattered beam accurately is high. A 'model recipe' is defined in which parameters are defined as either given ('fixed') or variable ('floating'). For floating parameters, the permitted range of variation is defined, either in absolute terms or by reference to deviation from a nominal value. In WO 2011-151121 (Aben), incorporated by reference herein in its entirety, it is described that it is for example also possible to impose relationships between floating parameters.

It is important the reconstruction provides a value of a parameter of interest (e.g. a CD) of the structure which is accurate as the reconstructed value is used to monitor and/or control the lithographic process. In general, the better the reconstructed value of the parameter of interest resembles the physical value of the parameter of interest the better the lithographic process can be monitored and/or controlled. It is known to assess a quality of reconstruction of a value of a parameter of interest of a structure by comparing the reconstructed value of the parameter of interest with a value of the parameter of interest obtained using a scanning electron microscope (SEM). However, this necessitates the availability of a scanning electron microscope. Also, as scanning electron microscopes are relatively slow it takes a long time to obtain the value of the parameter of interest using the scanning electron microscope. In addition, the value of the parameter of interest obtained using the scanning electron microscope may not always accurately resemble the physical value of the parameter of interest due to systems errors of the scanning electron microscope.

SUMMARY

It is an aim of the invention to provide an improved way of assessing a quality of reconstruction of a value of a parameter of interest of a structure. The inventors have recognized a way of assessing a quality of reconstruction of a value of a parameter of interest of a structure which does not require the use of a scanning electron microscope, by predicting values of the parameter of interest of structures using reconstructed values of parameters of structures, and by comparing the predicted values of the parameter of interest and the reconstructed values of the parameter of interest.

According to a first embodiment of the invention, there is provided a method of assessing a quality of reconstruction of a value of a parameter of interest of a structure, the method comprising: for each structure of a set of structures illuminating the structure with one or more beams of radiation and detecting a signal associated with the structure arising from interaction between the radiation and the structure; for each structure of the set of structures reconstructing, from the signal associated with the structure, values of parameters of a mathematical model of the structure, wherein at least one of the parameters is designated as the parameter of interest of the structure; predicting for each structure of the set of structures a value of the parameter of interest of the structure using at least a subset of the reconstructed values of the parameters associated with the set of structures; comparing the predicted values of the parameter of interest and the reconstructed values of the parameter of interest to assess the quality of reconstruction of a value of the parameter of interest of a structure.

The embodiment of the invention allows assessment of a quality of reconstruction of a value of a parameter of interest of a structure which does not require the use of a scanning electron microscope. Hence, the availability of an expensive scanning electron microscope is not required. Also, time is saved as the use of the slow scanning electron microscope is not required. Besides this, the inventors have recognized the invention provides a good way of assessing a quality of reconstruction of a value of a parameter of interest of a structure. The value of the parameter of interest obtained using the scanning electron microscope may however not always accurately resemble the physical value of the parameter of interest making use of the known method less reliable.

Without being bound to theory, a reason why the embodiment of the invention provides a reliable way of assessing a quality of reconstruction of a value of a parameter of interest of a structure may be because it is based on predictability. Before a value of a parameter of interest of a structure can be reconstructed the structure is illuminated with one or more beams of radiation and a signal is detected associated with the structure arising from interaction between the radiation and the structure. From the signal associated with the structure values of parameters of a mathematical model of the structure are reconstructed, wherein at least one of the parameters is designated as the parameter of interest of the structure. The signal associated with the structure is sensitive to a variation of multiple parameters of the structure. These parameters can be any descriptor of the structure. Often, the sensitivity of the signal to one parameter resembles the sensitivity of the signal to (a combination of) other parameters. This problem is referred to as correlation. Proper modeling and signal processing is used to separate the effect of different parameters in the signal. However, the inventors have seen that in practice some degree of correlation is still left. This deteriorates the accuracy, precision and speed of the measurement of the parameters, including the parameters in which the metrology user is interested. Hence, it is relevant to know if any correlation is present in the measurement. The inventors have recognized that if a measurement suffers from correlation, values of the parameters involved in the correlation change in unison. This implies that if correlation is present, the value of the parameter of interest can be predicted using values of other parameters. In general, the better a parameter can be predicted by values of other parameters the more correlation is present in the measurement. So, values of the parameter of interest are predicted using reconstructed values of other parameters, and the predicted values of the parameter of interest are compared with the reconstructed values of the parameter of interest to assess a quality of reconstruction of a value of a parameter of interest of a structure.

Another embodiment of the invention further provides an inspection apparatus for assessing a quality of reconstruction of a value of a parameter of interest of a structure, the apparatus comprising: an illumination system for illuminating each structure of a set of structures with one or more beams of radiation; a detection system for detecting for each structure of the set of structures a signal associated with the structure arising from interaction between the radiation and the structure; and a processor, wherein the processor is arranged to for each structure of the set of structures reconstruct, from the signal associated with the structure, values of parameters of a mathematical model of the structure, wherein at least one of the parameters is designated as the parameter of interest of the structure, wherein the processor is arranged to predict for each structure of the set of structures a value of the parameter of interest of the structure using at least a subset of the reconstructed values of the parameters associated with the set of structures, and wherein the processor is arranged to compare the predicted values of the parameter of interest and the reconstructed values of the parameter of interest to assess the quality of reconstruction of a value of the parameter of interest of a structure.

Another embodiment of the invention further provides a computer program product containing one or more sequences of machine-readable instructions for assessing a quality of reconstruction of a value of a parameter of interest of a structure, the instructions being adapted a use one or more processors to: for each structure of a set of structures receive a detected signal associated with the structure arising from interaction between radiation and the structure under predetermined illumination; for each structure of the set of structures reconstruct, from the signal associated with the structure, values of parameters of a mathematical model of the structure, wherein at least one of the parameters is designated as the parameter of interest of the structure; predict for each structure of the set of structures a value of the parameter of interest of the structure using at least a subset of the reconstructed values of the parameters associated with the set of structures; compare the predicted values of the parameter of interest and the reconstructed values of the parameter of interest to assess the quality of reconstruction of a value of the parameter of interest of a structure.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 3 illustrates the operating principles of a first scatterometer;

FIG. 4 illustrates the operating principles of a second scatterometer;

Figure 1:
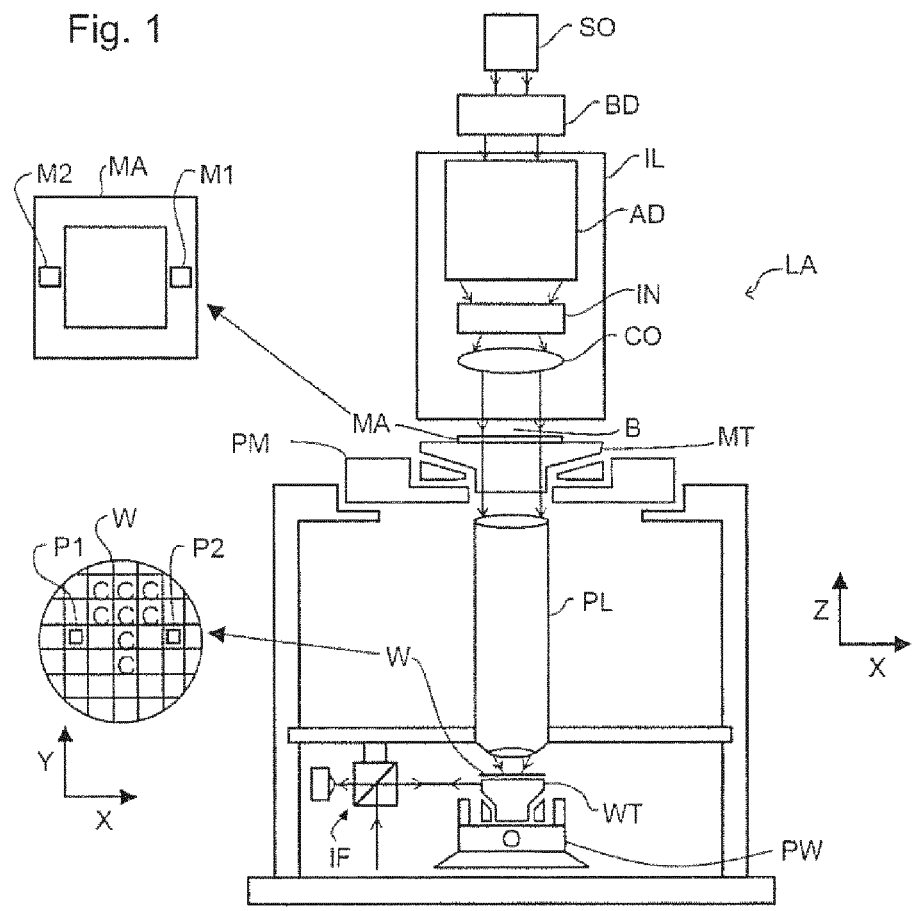
FIG. 1 is a schematic diagram of a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals, and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically shows a lithographic apparatus LAP including a source collector module SO according to an embodiment of the invention. The apparatus comprises: an illumination system (illuminator) IL configured to condition a radiation beam B (e.g., EUV radiation); a support structure (e.g., a mask table) MT constructed to support a patterning device (e.g., a mask or a reticle) MA and connected to a first positioner PM configured to accurately position the patterning device; a substrate table (e.g., a wafer table) WT constructed to hold a substrate (e.g., a resist-coated wafer) W and connected to a second positioner PW configured to accurately position the substrate; and a projection system (e.g., a reflective projection system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stages" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-) magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
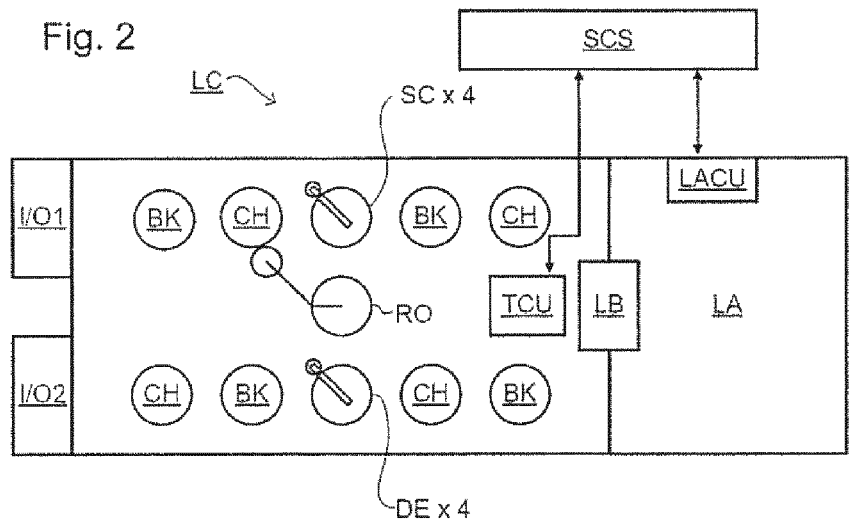
FIG. 2 is a schematic diagram of a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

FIG. 3 depicts a scatterometer which may be used in an embodiment of the present invention. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, as shown at the bottom of FIG. 3, the structure or profile z(x) giving rise to the detected spectrum I(λ) may be reconstructed by processing unit PU. This is conventionally done by Rigorous Coupled Wave Analysis (RCWA) and non-linear regression. It may be done by comparison with a library of simulated spectra. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Another scatterometer that may be used in an embodiment of the present invention is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters. In the following description, the term 'light' shall be used to refer to the radiation used in the scatterometry technique. Use of the term 'light' in relation to radiation used in scatterometry or any other metrology technique is not intended to imply any limitation to radiation in the visible part of the spectrum.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e. one with a wide range of light frequencies or wavelengths—and therefore of colors) is possible, which gives a large etendue, allowing the mixing of multiple wavelengths. Where a component in the broadband mix has a bandwidth of, say, $\Delta\lambda$, it can be advantageous to provide a spacing of at least 2 $\Delta\lambda$ (i.e. twice the bandwidth) between components. Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target 30 on substrate W may be a 1-D grating, which is printed such that after development, the bars are formed of solid resist lines. The target 30 may be a 2-D grating, which is printed such that after development, the grating is formed of solid resist pillars or vias (holes) in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

Using one of the scatterometers described above in combination with modeling of a target structure such as the target 30 and its diffraction properties, measurement of the shape and other parameters of the structure can be performed in a number of ways. In a first type of process, represented by FIG. 5, a diffraction pattern based on a first estimate of the target shape (a first candidate structure) is calculated and compared with the observed diffraction pattern. Parameters of the model are then varied systematically and the diffraction re-calculated in a series of iterations, to generate new candidate structures and so arrive at a best fit. In a second type of process, represented by FIG. 6, diffraction spectra for many different candidate structures are calculated in advance to create a 'library' of diffraction spectra. Then the diffraction pattern observed from the measurement target is compared with the library of calculated spectra to find a best fit. Both methods can be used together: a coarse fit can be obtained from a library, followed by an iterative process to find a best fit.

Figure 5:
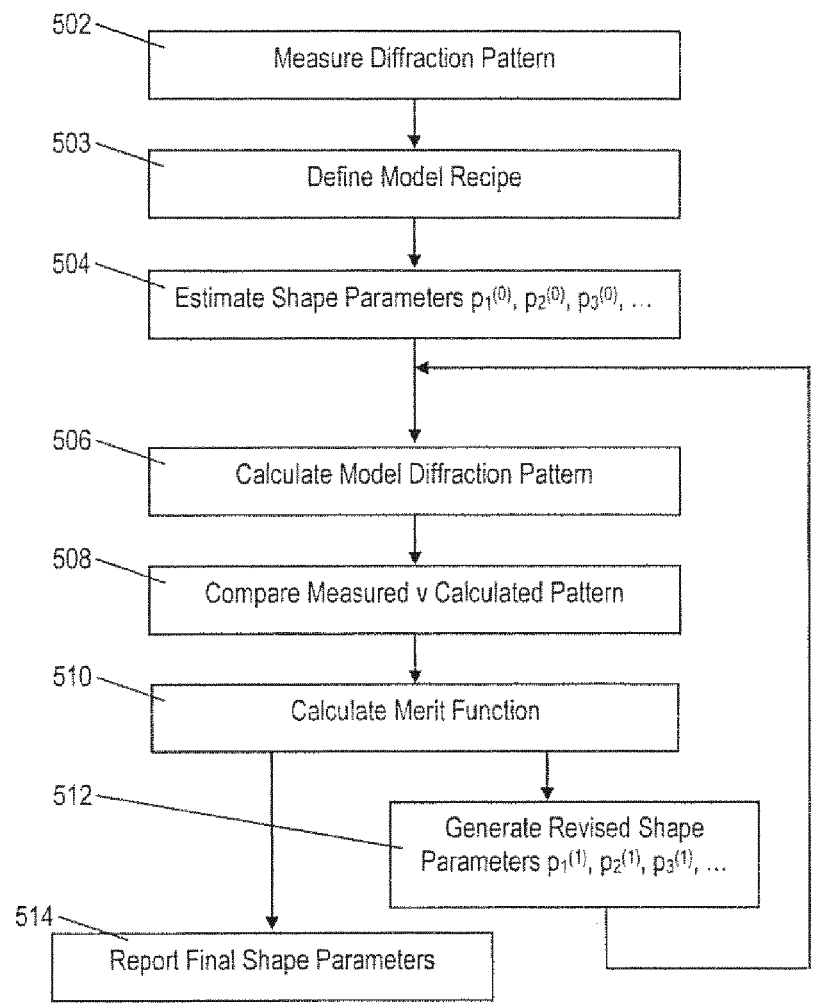
FIG. 5 depicts a first example process of reconstruction of a structure from scatterometer measurements.

Referring to FIG. 5 in more detail, the way the measurement of the target shape and/or material properties is carried out will be described in summary. The target will be assumed for this description to be a 1-dimensional (1-D) structure. In practice it may be 2-dimensional, and the processing will be adapted accordingly.

In step 502: The diffraction pattern of the actual target on the substrate is measured using a scatterometer such as those described above. This measured diffraction pattern is forwarded to a calculation system such as a computer. The calculation system may be the processing unit PU referred to above, or it may be a separate apparatus.

In step 503: A 'model recipe' is established which defines a parameterized model of the target structure in terms of a number of parameters $p_i$ ($p_1$, $p_2$, $p_3$ and so on). These parameters may represent for example, in a 1D periodic structure, the angle of a side wall, the height or depth of a feature, the width of the feature. Properties of the target material and underlying layers are also represented by parameters such as refractive index (at a particular wavelength present in the scatterometry radiation beam). Importantly, while a target structure may be defined by dozens of parameters describing its shape and material properties, the model recipe will define many of these to have fixed values, while others are to be variable or 'floating' parameters for the purpose of the following process steps. For the purposes of describing FIG. 5, only the variable parameters are considered as parameters $p_i$.

In step 504: A model target shape is estimated by setting initial values $p_i^{(0)}$ for the floating parameters (i.e. $p_1^{(0)}$, $p_2^{(0)}$, $p_3^{(0)}$ and so on). Each floating parameter will be generated within certain predetermined ranges, as defined in the recipe.

In step 506: The parameters representing the estimated shape, together with the optical properties of the different elements of the model, are used to calculate the scattering properties, for example using a rigorous optical diffraction method such as RCWA or any other solver of Maxwell equations. This gives an estimated or model diffraction pattern of the estimated target shape.

In steps 508, 510: The measured diffraction pattern and the model diffraction pattern are then compared and their similarities and differences are used to calculate a "merit function" for the model target shape.

In step 512: Assuming that the merit function indicates that the model needs to be improved before it represents accurately the actual target shape, new parameters $p_1^{(1)}$, $p_2^{(1)}$, $p_3^{(1)}$ etc. are estimated and fed back iteratively into step 506. Steps 506-512 are repeated.

In order to assist the search, the calculations in step 506 may further generate partial derivatives of the merit function, indicating the sensitivity with which increasing or decreasing a parameter will increase or decrease the merit function, in this particular region in the parameter space. The calculation of merit functions and the use of derivatives are generally known in the art, and will not be described here in detail.

In step 514: When the merit function indicates that this iterative process has converged on a solution with a desired accuracy, the currently estimated parameters are reported as the measurement of the actual target structure.

The computation time of this iterative process is largely determined by the forward diffraction model used, i.e. the calculation of the estimated model diffraction pattern using a rigorous optical diffraction theory from the estimated target structure. If more parameters are required, then there are more degrees of freedom. The calculation time increases in principle with the power of the number of degrees of freedom. The estimated or model diffraction pattern calculated at 506 can be expressed in various forms. Comparisons are simplified if the calculated pattern is expressed in the same form as the measured pattern generated in step 510. For example, a modeled spectrum can be compared easily with a spectrum measured by the apparatus of FIG. 3; a modeled pupil pattern can be compared easily with a pupil pattern measured by the apparatus of FIG. 4.

Throughout this description from FIG. 5 onward, the term 'diffraction pattern' will be used, on the assumption that the scatterometer of FIG. 4 is used. The skilled person can readily adapt the teaching to different types of scatterometer, or even other types of measurement instrument.

Figure 6:
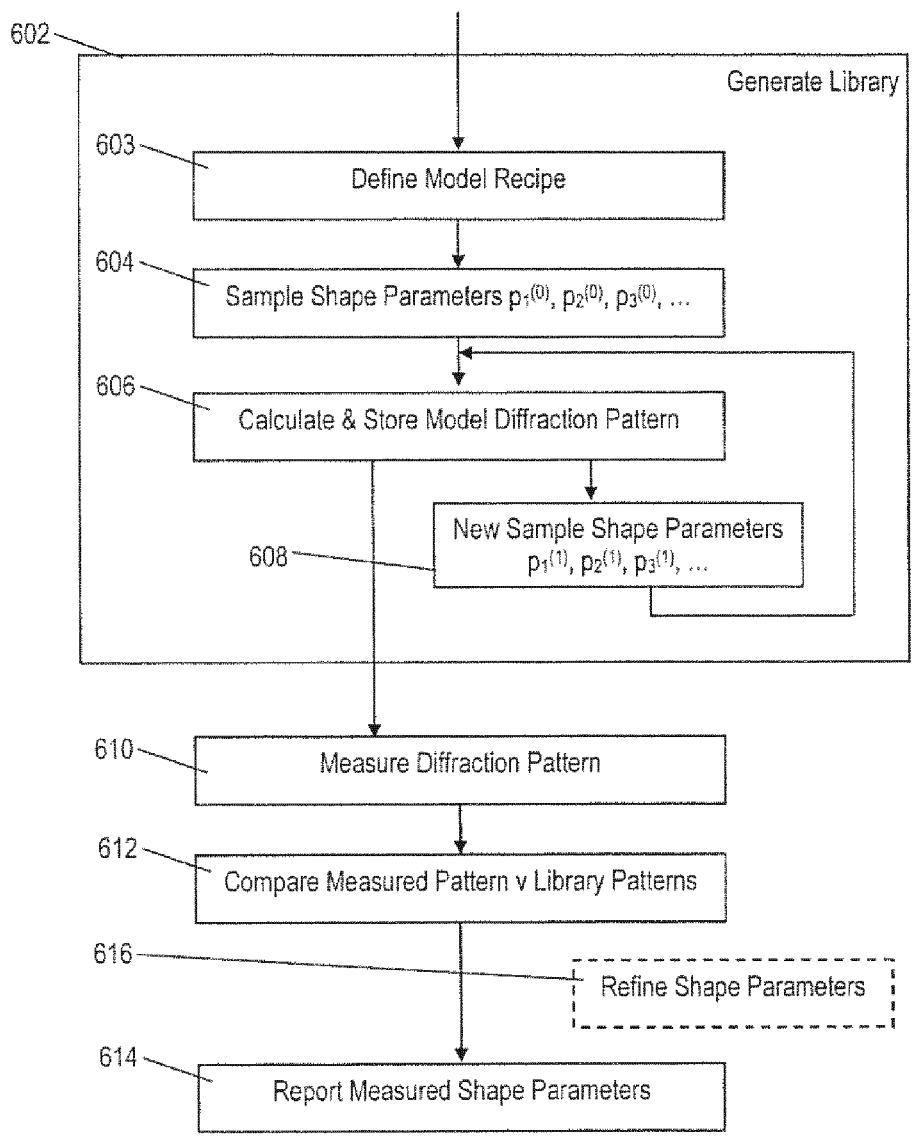
FIG. 6 depicts a second example process of reconstruction of a structure from scatterometer measurements.

FIG. 6 illustrates an alternative example process in which plurality of model diffraction patterns for different estimated target shapes (candidate structures) are calculated in advance and stored in a library for comparison with a real measurement. The underlying principles and terminology are the same as for the process of FIG. 5.

The steps of the FIG. 6 process are:

In step 602: The process of generating the library begins. A separate library may be generated for each type of target structure. The library may be generated by a user of the measurement apparatus according to need, or may be pre-generated by a supplier of the apparatus.

In step 603: A 'model recipe' is established which defines a parameterized model of the target structure in terms of a number of parameters $p_i$ ($p_1$, $p_2$, $p_3$ and so on). Considerations are similar to those in step 503 of the iterative process.

In step 604: A first set of parameters $p_1^{(0)}$, $p_2^{(0)}$, $p_3^{(0)}$, etc. is generated, for example by generating random values of all the parameters, each within its expected range of values.

In step 606: A model diffraction pattern is calculated and stored in a library, representing the diffraction pattern expected from a target shape represented by the parameters.

In step 608: A new set of shape parameters $p_1^{(1)}$, $p_2^{(1)}$, $p_3^{(1)}$, etc. is generated. Steps 606-608 are repeated tens, hundreds or even thousands of times, until the library which comprises all the stored modeled diffraction patterns is judged sufficiently complete. Each stored pattern represents a sample point in the multi-dimensional parameter space. The samples in the library should populate the sample space with a sufficient density that any real diffraction pattern will be sufficiently closely represented.

In step 610: After the library is generated (though it could be before), the real target 30 is placed in the scatterometer and its diffraction pattern is measured.

In step 612: The measured pattern is compared with the modeled patterns stored in the library to find the best matching pattern. The comparison may be made with every sample in the library, or a more systematic searching strategy may be employed, to reduce computational burden.

In step 614: If a match is found then the estimated target shape used to generate the matching library pattern can be determined to be the approximate object structure. The shape parameters corresponding to the matching sample are output as the measured shape parameters. The matching process may be performed directly on the model diffraction signals, or it may be performed on substitute models which are optimized for fast evaluation.

In step 616: Optionally, the nearest matching sample is used as a starting point, and a refinement process is used to obtain the final parameters for reporting. This refinement process may comprise an iterative process very similar to that shown in FIG. 5, for example.

Whether refining step 616 is needed or not is a matter of choice for the implementer. If the library is very densely sampled, then iterative refinement may not be needed because a good match will always be found. On the other hand, such a library might be too large for practical use. A practical solution is thus to use a library search for a coarse set of parameters, followed by one or more iterations using the merit function to determine a more accurate set of parameters to report the parameters of the target substrate with a desired accuracy. Where additional iterations are performed, it would be an option to add the calculated diffraction patterns and associated refined parameter sets as new entries in the library. In this way, a library can be used initially which is based on a relatively small amount of computational effort, but which builds into a larger library using the computational effort of the refining step 616. Whichever scheme is used, a further refinement of the value of one or more of the reported variable parameters can also be obtained based upon the goodness of the matches of multiple candidate structures. For example, the parameter values finally reported may be produced by interpolating between parameter values of two or more candidate structures, assuming both or all of those candidate structures have a high matching score.

Figure 7:
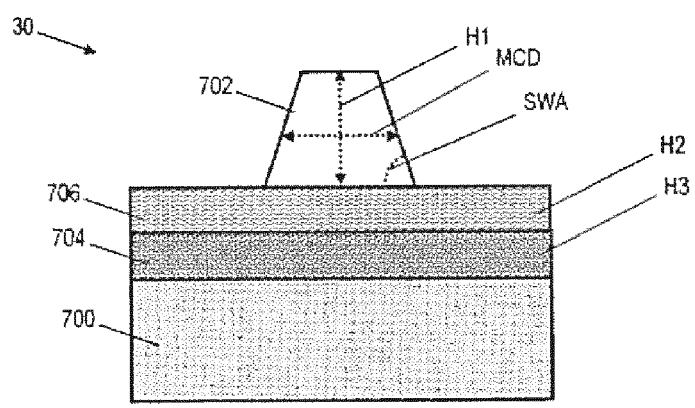
FIG. 7 is a schematic cross-section through an example structure to be measured by the process of FIG. 5 or FIG. 6, with associated model parameters.

FIG. 7 illustrates a very simple form of target 30, and some of the parameters that define its shape. A substrate 700, for example a silicon wafer, carries a diffraction grating formed by many parallel bars that have been formed by exposing and developing a layer of resist material. The target grating need not comprise raised bars, which are illustrated and mentioned as only an example. Suitable features include upstanding bars, contact holes, etc., that have been formed by lithography, or by lithography followed by etching, deposition and other process steps. Bars are chosen here purely for simplicity.

Feature 702 represents a cross section of one of the structures that make up the grating. Under the resist is a layer 704, which in a common example would be simply the 'native' oxide layer on a silicon wafer, for example having a thickness of 1 to 3 nm. In a real product, there may be many layers of different properties under the target 30. Prior to coating the substrate with resist and exposing, an anti-reflective BARC layer 706 has been coated on the substrate to improve the quality of the printed pattern, in a known manner.

Parameters of the feature 702, which are to be measured by a process such as shown in FIG. 5 or FIG. 6, include feature height H1, mid-height critical dimension (mid-CD or MCD) and side wall angle SWA. Other parameters can be defined if desired. SWA may be defined separately for left and right side walls, if asymmetries are to be measured. Any other features like top rounding, footing or a coating trapezoid accounting for Line Edge Roughness (LER) might be added to the model to increase accuracy.

These parameters H1, MCD, SWA will contribute in different ways to the diffraction pattern that will be observed when this target 30 is measured by scatterometry. Other shape parameters that will affect the diffraction pattern are the heights (thicknesses) of the underlying layers 706, 704, which are labeled H2, H3 respectively. In addition to geometrical parameters, optical parameters can be also included in the model. To model the target, and so permit the calculation of modeled diffraction patterns, estimated values for these parameters are used in the calculations of step 506 and/or 606. When one takes into account the number of layers, the shape parameters of the feature 702 and potentially also underlying features and layers, it becomes clear that the parameter space, in which the search for the best fitting parameter set is to be performed, is highly multi-dimensional. The target grating pattern itself may be two-dimensional. Additional parameters required for modeling are the properties of all the different materials, such as their refractive indices and extinction coefficients. These may be so well defined that they can be regarded as fixed parameters, or they may themselves be subject to uncertainties. They may need to be further subdivided according to the wavelength and polarization of the incoming radiation. In WO 2011-151121 (Aben), the contents of which are incorporated herein by reference in its entirety, it is described that it is for example also possible to impose relationships between floating parameters.

As mentioned above it is important the reconstruction provides a value of a parameter of interest (e.g. a CD) of the structure which is accurate as the reconstructed value is used to monitor and/or control the lithographic process. In general, the better the reconstructed value of the parameter of interest resembles the physical value of the parameter of interest the better the lithographic process can be monitored and/or controlled. It is known to assess a quality of reconstruction of a value of a parameter of interest of a structure by comparing the reconstructed value of the parameter of interest with a value of the parameter of interest obtained using a scanning electron microscope. As mentioned the inventors have recognized an improved way of assessing a quality of reconstruction of a value of a parameter of interest of a structure which does not require the use of a scanning electron microscope, by predicting values of the parameter of interest of structures using reconstructed values of parameters of structures and by comparing the predicted values of the parameter of interest and the reconstructed values of the parameter of interest.

Figure 8:
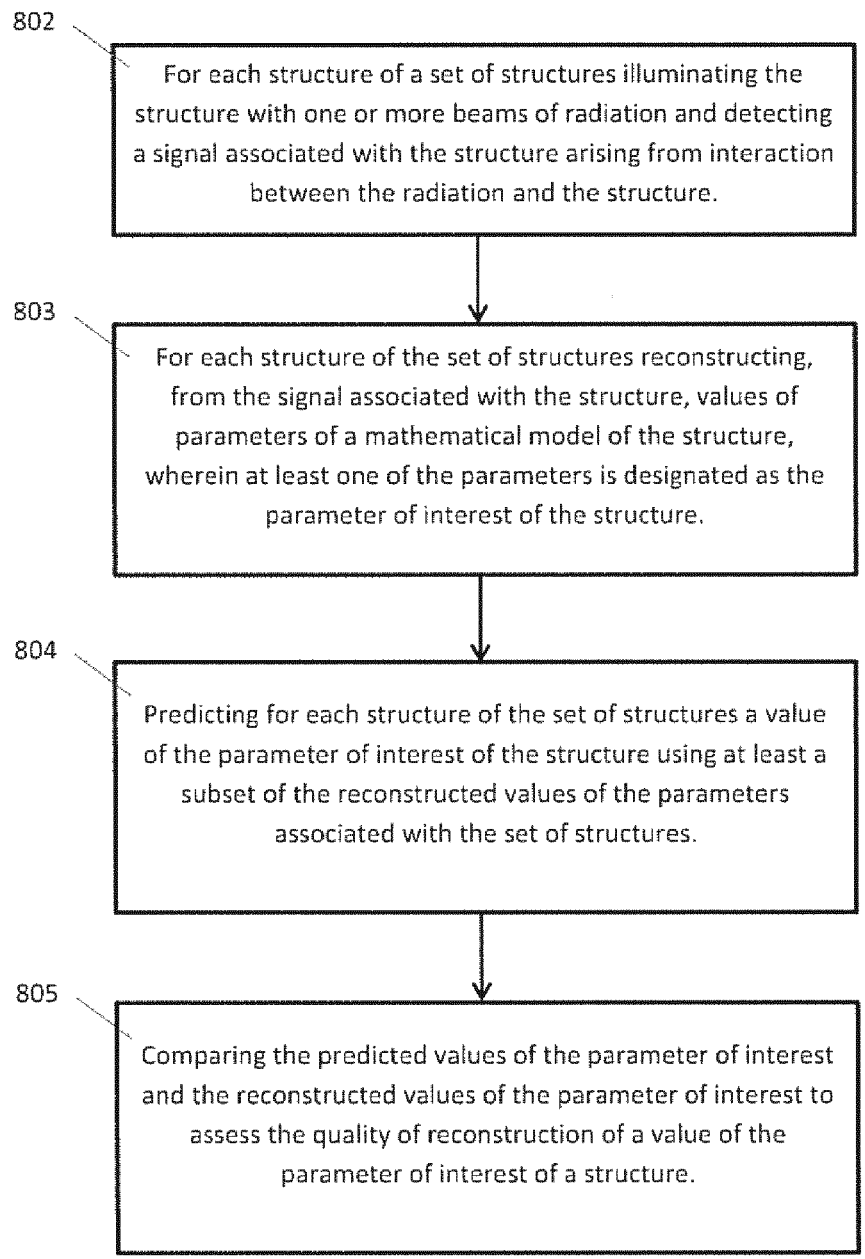
FIG. 8 illustrates a method of assessing a quality of reconstruction of a value of a parameter of interest of a structure, in accordance with an embodiment of the invention.

An embodiment according to the invention will now be described with reference to FIG. 8. FIG. 8 illustrates a method of assessing a quality of reconstruction of a value of a parameter of interest of a structure comprising the steps 802, 803, 804, and 805. The steps of the FIG. 8 method are:

In step 802: For each structure ($S_i$) of a set of (N) structures ($S_1, S_2, S_3, \ldots S_N$) illuminating the structure with one or more beams of radiation and detecting a signal associated with the structure arising from interaction between the radiation and the structure. In an embodiment the structures of the set of structures are present on a single substrate (it will be clear the structures of the set of structures may for example also be distributed over multiple substrates). Each structure may be illuminated with one or more beams of radiation using for example a scatterometer as described with reference to FIG. 3 or a scatterometer as described with reference to FIG. 4. These scatterometers can also be used for detecting for each structure a signal associated with the structure arising from interaction between the radiation and the structure. A single scatterometer may for example be used which successively addresses the structures $S_i$ (for example by moving the scatterometer from structure $S_1$ to structure $S_2$, from structure $S_2$ to structure $S_3$, and so on; in general to successively address the structures $S_i$ the scatterometer and the structures $S_i$ may be moved with respect to each other) and for each structure $S_i$ performs mentioned illuminating and detecting (it will be clear also two or more scatterometers may for example be used).

In step 803: For each structure of the set of structures reconstructing, from the signal associated with the structure, values of parameters of a mathematical model of the structure, wherein at least one of the parameters is designated as the parameter of interest of the structure. In an embodiment the reconstructing is performed by the processing unit PU of a type of scatterometer as described with reference to FIG. 3 or by the processing unit PU of a type of scatterometer as described with reference to FIG. 4. The parameters of the mathematical model of the structure may comprise parameters describing the shape and material properties of the structure. The parameters of the mathematical model of the structure may for example comprise one or more of a height, width or side wall angle of the structure. In an embodiment the parameter of interest of the structure is a width of the structure (it will be clear the parameter of interest of the structure may for example also be a height or side wall angle of the structure). As mentioned above for example a 'library based' and/or 'regression based' technique may be used for the reconstructing. Reconstruction is well known to a person skilled in the art and the person skilled in the art will have no difficulty in carrying out this reconstructing step.

In step 804: Predicting for each structure of the set of structures a value of the parameter of interest of the structure using at least a subset of the reconstructed values of the parameters associated with the set of structures. As an example, the reconstructed values of the parameter of interest obtained in step 803 are put in a vector. In mathematical form:

$$\vec{m} = \begin{bmatrix} m_1 \\ m_2 \\ \ldots \\ m_N \end{bmatrix}$$

where $\vec{m}$ represents the vector containing the reconstructed values of the parameter of interest and each element $m_i$ of vector $\vec{m}$ represents the reconstructed value of the parameter of interest for the associated structure $S_i$. Proceeding with the example, the remaining reconstructed values of the parameters associated with the set of structures (e.g. in this example the reconstructed values of the parameters associated with the set of structures excluding the reconstructed values of the parameter of interest) obtained in step 803 are put in a matrix. In mathematical form:

$$X = \begin{bmatrix} x_{1,a} & x_{1,b} & \ldots & x_{1,M} & 1 \\ x_{2,a} & x_{2,b} & \ldots & x_{2,M} & 1 \\ \vdots & \vdots & \ddots & \vdots & 1 \\ x_{N,a} & x_{N,b} & \ldots & x_{N,M} & 1 \end{bmatrix}$$

where X represents the matrix containing the remaining reconstructed values of the parameters associated with the set of structures plus an extra column with ones to remove the mean in the computation (given below). In this example each column (excluding the last column with ones) contains the reconstructed values of a particular parameter. For example each element $x_{i,a}$ of the first column represents the reconstructed value of the parameter 'a' for the associated structure $S_i$, and each element $x_{i,b}$ of the second column represents the reconstructed value of the parameter 'b' for the associated structure $S_i$, etcetera. In this example the set of structures consists of N structures and the number of remaining parameters is M. As an example the parameter of interest of the structure is a width of the structure, parameter 'a' of the structure is a height of the structure, and parameter 'b' of the structure is a side wall angle of the structure. Proceeding with the example, matrix X and vector $\vec{m}$ are now used to predict for each structure $S_i$ of the set of N structures a value of the parameter of interest of the structure $S_i$. In this example the predicting uses means of linear regression analysis. In mathematical form:

$$\hat{\vec{m}} = X(X^T X)^{-1} X^T \vec{m}$$

where $\hat{\vec{m}}$ represents the vector containing the predicted values of the parameter of interest and each element $\hat{m}_i$ of vector $\hat{\vec{m}}$ represents the predicted value of the parameter of interest for the associated structure $S_i$. The predicting as mentioned above can for example be performed by the processing unit PU of a type of scatterometer as described with reference to FIG. 3 or by the processing unit PU of a type of scatterometer as described with reference to FIG. 4 by configuring the processing unit PU to perform mentioned predicting. Alternatively or additionally the supervisory control system SCS and/or the lithography control unit LACU may be configured to perform the predicting.

In step 805: Comparing the predicted values of the parameter of interest and the reconstructed values of the parameter of interest to assess the quality of reconstruction of a value of the parameter of interest of a structure. Proceeding with the example in an embodiment the comparing uses the standard deviation. In mathematical form:

$$Q = \frac{\sqrt{\frac{1}{N} \sum_{i=1}^{i=N} (m_i - \hat{m}_i)^2}}{std(\vec{m})}$$

where Q is a single value being a metric of the quality of reconstruction of a value of the parameter of interest of a structure and std stands for standard deviation. The comparing according to the example uses a standard deviation of the reconstructed values of the parameter of interest for normalization. Following the example Q is a number between 0 and 1. In case it is possible to accurately predict the reconstructed values of the parameter of interest, the numerator corresponds to a small number and the value of Q is close to zero. In case it is not possible to accurately predict the reconstructed values of the parameter of interest, the numerator is close to std($\vec{m}$) and the value of Q is close to one. Generally, the quality of reconstruction of a value of the parameter of interest of a structure is assessed as higher with increasing dissimilarity (or, the differently, with decreasing similarity) between the predicted values of the parameter of interest and the reconstructed values of the parameter of interest (following the example a higher quality of reconstruction would mean a value of Q closer to one). The comparing as mentioned above can for example be performed by the processing unit PU of a type of scatterometer as described with reference to FIG. 3 or by the processing unit PU of a type of scatterometer as described with reference to FIG. 4 by configuring the processing unit PU to perform mentioned comparing. Alternatively or additionally the supervisory control system SCS and/or the lithography control unit LACU may be configured to perform the comparing.

The method of assessing a quality of reconstruction of a value of a parameter of interest of a structure described above with reference to FIG. 8 is an example and many variations to this example are possible. Generally, a method of assessing a quality of reconstruction of a value of a parameter of interest of a structure may comprise the steps of for each structure of a set of structures illuminating the structure with one or more beams of radiation and detecting a signal associated with the structure arising from interaction between the radiation and the structure; for each structure of the set of structures reconstructing, from the signal associated with the structure, values of parameters of a mathematical model of the structure, wherein at least one of the parameters is designated as the parameter of interest of the structure; predicting for each structure of the set of structures a value of the parameter of interest of the structure using at least a subset of the reconstructed values of the parameters associated with the set of structures; and comparing the predicted values of the parameter of interest and the reconstructed values of the parameter of interest to assess the quality of reconstruction of a value of the parameter of interest of a structure.

In an embodiment the reconstructing values of parameters of a mathematical model of the structure is in accordance with a model recipe. As described above in a model recipe parameters may for example be defined as either given ('fixed') or variable ('floating'). For floating parameters, the permitted range of variation may for example be defined, either in absolute terms or by reference to deviation from a nominal value. As mentioned, in WO 2011-151121 (Aben) it is described that it is for example also possible to impose relationships between floating parameters. In an embodiment, regarding the reconstructing step, the parameters of a mathematical model of the structure of which the values are reconstructed are defined as variable ('floating').

As described with reference to 803 of FIG. 8 the reconstructing may use a library based and/or regression based technique. In addition or alternatively the reconstructing may use a machine learning based and/or support vector machine based technique or any other suitable technique.

In an embodiment the predicting uses means of regression analysis, for example means of linear regression analysis (see for example step 804 above described with reference to FIG. 8), although any suitable means of analysis may be used. In an embodiment the predicting uses means of non-linear regression analysis.

In an embodiment, regarding the comparing, the quality of reconstruction of a value of the parameter of interest of a structure is assessed as higher with increasing dissimilarity (or, the differently, with decreasing similarity) between the predicted values of the parameter of interest and the reconstructed values of the parameter of interest. In an embodiment the quality of reconstruction of a value of the parameter of interest of a structure is assessed as lower with decreasing dissimilarity (or, the differently, with decreasing similarity) between the predicted values of the parameter of interest and the reconstructed values of the parameter of interest. The dissimilarity (or, the differently, the similarity) between the predicted values of the parameter of interest and the reconstructed values of the parameter of interest may be calculated using for example the formulas as described above with reference to FIG. 8.

In an embodiment, an example of which is described above with reference to FIG. 8, the output of the comparing the predicted values of the parameter of interest and the reconstructed values of the parameter of interest is a single value, the single value being a metric of the quality of reconstruction of a value of the parameter of interest of a structure. Alternatively, the output of the comparing the predicted values of the parameter of interest and the reconstructed values of the parameter of interest is set of values, the set of values being a metric of the quality of reconstruction of a value of the parameter of interest of a structure. For example, the predicted values of the parameter of interest may be divided over multiple sets as are the associated reconstructed values of the parameter of interest. The comparing may then for example be performed for each of the multiple sets separately each resulting in a value of the set of values. The value associated with a particular set of the multiple sets is a metric of the quality of reconstruction of a value of the parameter of interest of a structure for that particular set. For example, the dividing of the predicted values of the parameter of interest and the associated reconstructed values of the parameter of interest over multiple sets may be based on the location of the structures of the set of structures. For example each set may be associated with a particular location of the structures of the set of structures on the substrate. In case the substrate is divided in four quadrants each quadrant may have an associated set comprising the structures of the set of structures which are located on that quadrant of the substrate. In this way the output of the comparing the predicted values of the parameter of interest and the reconstructed values of the parameter of interest is set of four values, each value being a metric of the quality of reconstruction of a value of the parameter of interest of a structure for its associated quadrant. It will be clear the predicted values of the parameter of interest may instead be divided differently over multiple sets as are the associated reconstructed values of the parameter of interest.

In the example as described above with reference to step 805 of FIG. 8 the comparing uses a standard deviation of the reconstructed values of the parameter of interest for normalization. Alternatively, in an embodiment the comparing uses a standard deviation of $\hat{\vec{m}}$. In a further embodiment the comparing uses a normalization based upon the reconstructed values of the parameter of interest. In a further embodiment the comparing uses a normalization based upon $\hat{\vec{m}}$. As will be apparent to one skilled in the art the predicted values of the parameter of interest and the reconstructed values of the parameter of interest can also be compared in other ways.

In an embodiment the predicting uses mean centered values of the at least the subset of the reconstructed values of the parameters associated with the set of structures. As described above with reference to FIG. 8, in particular the predicting step 804, using mean centered values may be implemented by the column with ones (or any other suitable non-zero value) in matrix X. As mentioned this removes the mean in the computation. More general, in an embodiment the predicting uses a common mode suppression of the at least the subset of the reconstructed values of the parameters associated with the set of structures.

In an embodiment the parameters of the mathematical model of the structure comprise parameters describing material properties of the structure, like the refractive index and/or extinction coefficient of a material of the structure.

In an embodiment the parameter of interest of the structure is a CD of the structure, preferably the mCD of the structure. It will be clear also another parameter may be designated as the parameter of interest of the structure and the choice will depend on the parameter the user is interested in.

In an embodiment the number of parameters of the mathematical model of the structure is greater than 4, or 8, or 16, or 32. In an embodiment the number of parameters of the mathematical model of the structure is greater than 64, or 128.

In an embodiment each structure of the set of structures is formed by lithography, for example using the lithographic apparatus as described above with reference to FIG. 1. The structures may for example also be formed by imprint lithography or electron beam lithography, or by any other suitable way.

In an embodiment each structure of the set of structures is a dedicated metrology target. A dedicated metrology target may for example be a metrology target designed for CD, and/or focus metrology. In another embodiment each structure of the set of structures is part of the product (e.g. IC) itself. A combination where some of the structures of the set of structures are dedicated metrology targets and the other structures of the set of structures are part of the product is also a possibility. It will be clear also other types of structures may be used. Also, in an embodiment the structures of the set of structures are essentially identical by design. In another embodiment at least some of the structures of the set structures are different by design.

In an embodiment the number of structures in the set of structures is greater than 5, or 20, or 100, or 1000. Any suitable number of structures may be used.

In an embodiment the structures of the set of structures are present on a single substrate. In another embodiment the structures of the set of structures a divided over more than one substrate.

In an embodiment the predicting step is performed first followed by the comparing step. It will however be clear to a person skilled in the art that it is also possible the predicting and the comparing are for example performed essentially in a same mathematical step. Referring to the example described above with reference to FIG. 8 the predicting and the comparing may for example be performed essentially in a same mathematical step by incorporating the formulae of the predicting step 804 into the formula of the comparing step 805. The predicting and the comparing can for example be performed essentially in a same mathematical step by the processing unit PU of a type of scatterometer as described with reference to FIG. 3 or by the processing unit PU of a type of scatterometer as described with reference to FIG. 4 by configuring the processing unit PU to perform mentioned predicting and comparing essentially in a same mathematical step. Alternatively or additionally the supervisory control system SCS and/or the lithography control unit LACU may be configured to perform the predicting and the comparing essentially in a same mathematical step.

In an embodiment wherein the reconstructing values of parameters of a mathematical model of the structure is in accordance with a model recipe, the method may further comprise repeating the method multiple times each time using a different model recipe. For example, the method may be repeated once, or 2, 4, 8, 16, 32, or 64 times, or more times. The difference in the model recipes used may for example be in which parameters are defined as given ('fixed') and which parameters are defined as variable ('floating'). Alternatively or additionally the difference in the model recipes used may for example be in the permitted range of variation of the floating parameters. Alternatively or additionally the difference in the model recipes used may for example be in the number of parameters of the mathematical model of the structure. Alternatively or additionally the difference in the model recipes used may for example be in the type of parameters of the mathematical model of the structure (for example the first time a width of the structure is used as a parameter of the mathematical model of the structure and not a height of the structure, and the second time a height of the structure is used as a parameter of the mathematical model of the structure and not a width of the structure). In an embodiment the step of for each structure of a set of structures illuminating the structure with one or more beams of radiation and detecting a signal associated with the structure arising from interaction between the radiation and the structure is performed once and the reconstructing, predicting and comparing steps are performed for each different model recipe (each time reusing the for each structure of the set of structures detected signal associated with the structure).

Further to the above, in an embodiment the method further comprises determining a model recipe from the different model recipes used in the method which has, compared to other model recipes used in the method, a high quality of reconstruction of a value of the parameter of interest of a structure. For example, for each different model recipe used in the method the value of Q as described above with reference to 805 of FIG. 8 may be determined. Following the example, as a higher quality of reconstruction means a value of Q closer to one, a model recipe can be determined from the different model recipes used in the method which has, compared to other model recipes used in the method, a value of Q close to 1. In this way a preferred model recipe can be determined without the use of a scanning electron microscope. The determination may for example be executed by a processing unit. Alternatively the determination may for example be left to a user being presented with the value of Q for each different model recipe.

In an embodiment the mathematical model of the structure and the parameter of interest of the structure are the same during each repetition of the method (but each time a different model recipe may be used). In an embodiment the mathematical model of the structure differs during each repetition of the method. In an embodiment the mathematical model of the structure is the same during each repetition of the method. In an embodiment the parameter of interest of the structure is the same during each repetition of the method.

In an embodiment wherein the reconstructing values of parameters of a mathematical model of the structure is in accordance with a model recipe, the method may further comprise altering the model recipe based on the assessment of the quality of reconstruction of a value of the parameter of interest of a structure.

Although the predicting for each structure of the set of structures a value of the parameter of interest of the structure may use a full set of the reconstructed values of the parameters associated with the set of structures, using a subset of the reconstructed values is also a possibility as will be clear to the person skilled in the art. For example, in case the reconstructing provides reconstructed values of a side wall angle it may not be a necessity these reconstructed values of a side wall angle are actually used in the predicting step. These reconstructed values of a side wall angle may however in an embodiment be used in the predicting step.

Although in the reconstructing step one of the parameters may be designated as the parameter of interest of the structure, it is also possible two or more of the parameters are designated as the parameters of interest of the structure. For example, in case two of the parameters are designated as the parameters of interest, the predicting and the comparing steps may for example be performed for each of the parameters of interest.

The term "for each structure of a set of structures" as used throughout the text to describe the invention encompasses all possible implementations of the invention as will be apparent to one skilled in the art. "For each structure of a set of structures" encompasses for example the implementation where the steps of reconstructing 803 and predicting 804 are performed for each structure which has undergone the step of illuminating 802. "For each structure of a set of structures" also encompasses for example the implementation where the steps of reconstructing 803 and predicting 804 are not performed for each structure which has undergone the step of illuminating 802. "For each structure of a set of structures" also encompasses for example the implementation where the step of reconstructing 803 is performed for each structure which has undergone the step of illuminating 802. "For each structure of a set of structures" also encompasses for example the implementation where the step of reconstructing 803 is not performed for each structure which has undergone the step of illuminating 802. "For each structure of a set of structures" also encompasses for example the implementation where the step of predicting 804 is performed for each structure which has undergone the step of reconstructing 803. "For each structure of a set of structures" also encompasses for example the implementation where the step of predicting 804 is not performed for each structure which has undergone the step of reconstructing 803.

As will be clear to the person skilled in the art at least part of the embodiments of the invention described may for example be executed by a processor, e.g. a processor of the processing unit PU of a type of scatterometer as described with reference to FIG. 3 or by a processor of the processing unit PU of a type of scatterometer as described with reference to FIG. 4 by arranging the processor to perform these parts of the embodiments. Alternatively or additionally a processor of the supervisory control system SCS and/or a processor of the lithography control unit LACU may for example be arranged to perform these parts of the embodiments. For example, embodiments described in relation to the reconstructing, predicting, and/or comparing may be executed by a processor.

As will be clear to the person skilled in the art embodiments of the invention described may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

For example, embodiments of the present invention may be implemented by implementing at least part of the methods described herein by a processor to provide an inspection apparatus for assessing a quality of reconstruction of a value of a parameter of interest of a structure.

For example, the invention provides an inspection apparatus for assessing a quality of reconstruction of a value of a parameter of interest of a structure, the apparatus comprising: an illumination system for illuminating each structure of a set of structures with one or more beams of radiation; a detection system for detecting for each structure of the set of structures a signal associated with the structure arising from interaction between the radiation and the structure; and a processor, wherein the processor is arranged to for each structure of the set of structures reconstruct, from the signal associated with the structure, values of parameters of a mathematical model of the structure, wherein at least one of the parameters is designated as the parameter of interest of the structure, wherein the processor is arranged to predict for each structure of the set of structures a value of the parameter of interest of the structure using at least a subset of the reconstructed values of the parameters associated with the set of structures, and wherein the processor is arranged to compare the predicted values of the parameter of interest and the reconstructed values of the parameter of interest to assess the quality of reconstruction of a value of the parameter of interest of a structure. As will be clear to the person skilled in the art at least part of the embodiments of the invention described may be implemented by arranging the processor to implement at least part of the embodiments of the invention described.

The processor (may be more than one) may operate with a computer program product containing one or more sequences of machine-readable instructions for assessing a quality of reconstruction of a value of a parameter of interest of a structure, the instructions being adapted to cause one or more processors to perform the methods described herein.

For example, the invention provides a computer program product containing one or more sequences of machine-readable instructions for assessing a quality of reconstruction of a value of a parameter of interest of a structure, the instructions being adapted to cause one or more processors to: for each structure of a set of structures receive a detected signal associated with the structure arising from interaction between radiation and the structure under predetermined illumination; for each structure of the set of structures reconstruct, from the signal associated with the structure, values of parameters of a mathematical model of the structure, wherein at least one of the parameters is designated as the parameter of interest of the structure; predict for each structure of the set of structures a value of the parameter of interest of the structure using at least a subset of the reconstructed values of the parameters associated with the set of structures; compare the predicted values of the parameter of interest and the reconstructed values of the parameter of interest to assess the quality of reconstruction of a value of the parameter of interest of a structure.

An example of results of an implementation of the invention of assessing a quality of reconstruction of a value of a parameter on interest of a structure is now described with reference to FIG. 9. This is an example of results of an implementation of the invention only and many variations to this implementation of the invention are possible as described throughout the text.

Some specifics regarding this particular example are given first. The parameter of interest of the structure is a mCD of the structure. The number of structures in the set of structures is 173 and the structures of the set of structures are present on a single substrate. Each structure of the set of structures was formed by lithography and is a dedicated metrology target. The structures of the set of structures are essentially identical by design. The reconstructing used a regression based technique. The predicting used means of linear regression analysis and mean centered values of the reconstructed values of the parameters associated with the set of structures. The predicting used the formulae described above with reference to 804 of FIG. 8 for calculating the vector containing the predicted values of the parameter of interest $\vec{m}$. The comparing used a standard deviation of the reconstructed values of the parameter of interest for normalization. The comparing used the formula described above with reference to 805 of FIG. 8 for calculating a single value Q being a metric of the quality of reconstruction of a value of the parameter of interest of a structure. The output of the comparing was a single value being a metric of the quality of reconstruction of a value of the parameter of interest of a structure.

In this particular example the method of assessing a quality of reconstruction of a value of a parameter of interest of a structure was repeated ten times each time using a different model recipe. The step of for each structure of a set of structures illuminating the structure with one or more beams of radiation and detecting a signal associated with the structure arising from interaction between the radiation and the structure was performed once and the reconstructing, predicting and comparing steps were performed for each different model recipe. The mathematical model of the structure and the parameter of interest of the structure were the same during each repetition of the method.

Figure 9:
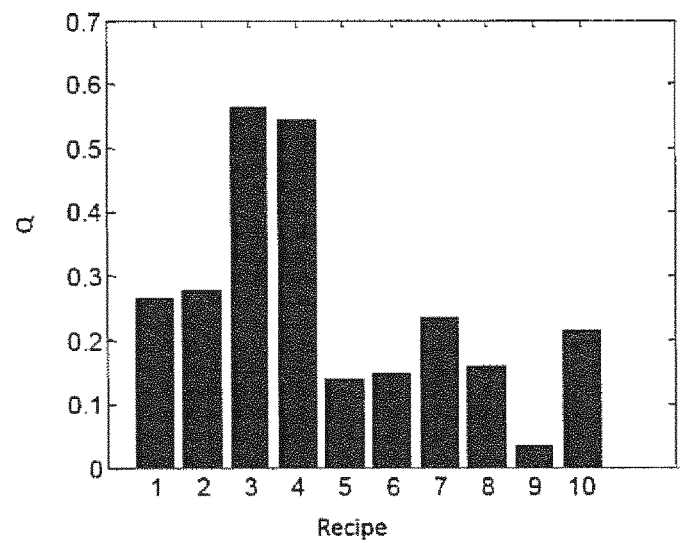
FIGS. 9(a) and 9(b) provide an example of results of an implementation of the invention of assessing a quality of reconstruction of a value of a parameter on interest of a structure.

FIG. 9(*a*) presents the value of Q, being a metric of the quality of reconstruction of a value of the parameter of interest of a structure, for each of the ten different model recipes used. As described above with reference to 805 of FIG. 8 in this example Q is a number between 0 and 1. In case it is possible to predict the reconstructed values of the parameter of interest well the value of Q is close to zero. In case it is not possible to predict the reconstructed values of the parameter of interest well the value of Q is close to one. Generally, the quality of reconstruction of a value of the parameter of interest of a structure is assessed as higher with increasing dissimilarity (or, the differently, with decreasing similarity) between the predicted values of the parameter of interest and the reconstructed values of the parameter of interest. Following the example a higher quality of reconstruction would mean a value of Q closer to one. From FIG. 9(*a*) it can be seen that using recipe 3 resulted in the highest value of Q, followed by recipe 4. Recipe 9 resulted in the lowest value of Q, followed by recipe 5. Hence, a quality of reconstruction of the mCD of the structure was assessed as higher when recipe 3 or recipe 4 was used compared to when for example recipe 9 or recipe 5 was used.

The left column of FIG. 9(*b*) shows the ranking of the ten different model recipes used based on the value of Q. To validate the results a comparison has been made with results obtained by using a scanning electron microscope (SEM). The SEM was used to physically measure the mCD of the structure. A quality of reconstruction of a value of the mCD of the structure was again assessed for each of the ten different model recipes used, but now by, for each different model recipe, comparing the measured value of the mCD of the structure obtained by SEM and the reconstructed values of the mCD. The right column of FIG. 9(*b*) shows the ranking of the ten different model recipes used based on the comparing the measured value of the mCD of the structure obtained by SEM and the reconstructed values of the mCD. A quality of reconstruction of the mCD of the structure was assessed as higher with increasing similarity between the measured value of the mCD of the structure obtained by SEM and the reconstructed values of the mCD. As can be seen the ranking obtained by using the invention (left column) has good consistency with the ranking obtained by using SEM (right column). According to both methods using recipes 3, 4, 2, and 1 resulted in a high quality of reconstruction of a value of the mCD of the structure compared to the other model recipes use, validating the results obtained by the method according to the invention. Hence, the invention provides a way of assessing a quality of reconstruction of a value of a parameter of interest of a structure which does not require the use of a scanning electron microscope.

Although specific reference may be made in this text to the use of inspection methods and apparatus in the manufacture of ICs, it should be understood that the inspection methods and apparatus described herein may have other applications, such as the manufacture of integrated optical systems, guidance and detection patterns for magnetic domain memories, flat-panel displays, reticles, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The term "electromagnetic" encompasses electric and magnetic.

The term "electromagnetic scattering properties" encompasses reflection and transmission coefficients and scatterometry measurement parameters including spectra (such as intensity as a function of wavelength), diffraction patterns (intensity as a function of position/angle) and the relative intensity of transverse magnetic- and transverse electric-polarized light and/or the phase difference between the transverse magnetic- and transverse electric-polarized light. Diffraction patterns themselves may be calculated for example using reflection coefficients.

Thus, although embodiments of the present invention are described in relation to reflective scattering, the invention is also applicable to transmissive scattering.

While specific embodiments of the invention have been described above, it will be appreciated that the invention may be practiced otherwise than as described. For example, the invention may take the form of a computer program product containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the spirit and scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of assessing a quality of reconstruction of a value of a parameter of interest of a structure, the method comprising:
    for each structure of a set of structures illuminating the structure with one or more beams of radiation and detecting a signal associated with the structure arising from interaction between the radiation and the structure;
    for each structure of the set of structures reconstructing, from the signal associated with the structure, values of parameters of a mathematical model of the structure, wherein at least one of the parameters is designated as the parameter of interest of the structure;
    predicting for each structure of the set of structures a value of the parameter of interest of the structure using at least a subset of the reconstructed values of the parameters associated with the set of structures; and
    comparing the predicted values of the parameter of interest and the reconstructed values of the parameter of interest to assess the quality of reconstruction of a value of the parameter of interest of a structure.

2. The method of claim 1, wherein the reconstructing values of parameters of a mathematical model of the structure are in accordance with a model recipe.

3. The method of claim 1, wherein the predicting uses means of regression analysis.

4. The method of claim 1, wherein the comparing the quality of reconstruction of a value of the parameter of interest of a structure is assessed as higher with increasing dissimilarity between the predicted values of the parameter of interest and the reconstructed values of the parameter of interest.

5. The method of claim 1, wherein the output of the comparing the predicted values of the parameter of interest and the reconstructed values of the parameter of interest is a single value, the single value being a metric of the quality of reconstruction of a value of the parameter of interest of a structure.

6. The method of claim 1, wherein the comparing uses a normalization based upon the reconstructed values of the parameter of interest.

7. The method of claim 1, wherein the predicting uses a common mode suppression of the at least the subset of the reconstructed values of the parameters associated with the set of structures.

8. The method of claim 1, wherein the parameters of the mathematical model of the structure comprise parameters describing the shape and material properties of the structure.

9. The method of claim 1, wherein the number of parameters of the mathematical model of the structure is greater than 4, or 8, or 16 or 32.

10. The method of any preceding claim 1, wherein the number of structures in the set of structures is greater than 5, or 20, or 100, or 1000.

11. The method of claim 1, wherein the structures of the set of structures are essentially identical by design.

12. The method of claim 2, the method further comprising repeating the method multiple times each time using a different model recipe.

13. The method according to claim 12, wherein the step of for each structure of a set of structures illuminating the structure with one or more beams of radiation and detecting a signal associated with the structure arising from interaction between the radiation and the structure is performed once and the reconstructing, predicting and comparing steps are performed for each different model recipe.

14. The method according to claim 12, wherein the mathematical model of the structure and the parameter of interest of the structure are the same during each repetition of the method.

15. The method according to claim 12, further comprising determining a model recipe from the different model recipes used in the method which has, compared to other model recipes used in the method, a high quality of reconstruction of a value of the parameter of interest of a structure.

16. The method of claim 1, wherein the predicting and the comparing are performed essentially in a same mathematical step.

17. The method of claim 2, the method further comprising altering the model recipe based on the assessment of the quality of reconstruction of a value of the parameter of interest of a structure.

18. An inspection apparatus for assessing a quality of reconstruction of a value of a parameter of interest of a structure, the apparatus comprising:

an illumination system configured to illuminate for illuminating each structure of a set of structures with one or more beams of radiation;

a detection system configured to detect for each structure of the set of structures a signal associated with the structure arising from interaction between the radiation and the structure; and a processor, wherein the processor is arranged to for each structure of the set of structures reconstruct, from the signal associated with the structure, values of parameters of a mathematical model of the structure, wherein at least one of the parameters is designated as the parameter of interest of the structure, wherein the processor is arranged to predict for each structure of the set of structures a value of the parameter of interest of the structure using at least a subset of the reconstructed values of the parameters associated with the set of structures, and wherein the processor is arranged to compare the predicted values of the parameter of interest and the reconstructed values of the parameter of interest to assess the quality of reconstruction of a value of the parameter of interest of a structure.

19. A computer program product containing one or more sequences of machine-readable instructions for assessing a quality of reconstruction of a value of a parameter of interest of a structure, the instructions being adapted to cause one or more processors to:

for each structure of a set of structures receive a detected signal associated with the structure arising from interaction between radiation and the structure under predetermined illumination;

for each structure of the set of structures reconstruct, from the signal associated with the structure, values of parameters of a mathematical model of the structure, wherein at least one of the parameters is designated as the parameter of interest of the structure;

predict for each structure of the set of structures a value of the parameter of interest of the structure using at least a subset of the reconstructed values of the parameters associated with the set of structures; and compare the predicted values of the parameter of interest and the reconstructed values of the parameter of interest to assess the quality of reconstruction of a value of the parameter of interest of a structure.

* * * * *

UNITED STATES PATENT AND TRADEMARK OFFICE
CERTIFICATE OF CORRECTION

PATENT NO. : 9,760,018 B2  
APPLICATION NO. : 14/906898  
DATED : September 12, 2017  
INVENTOR(S) : Mossavat et al.

Page 1 of 1

It is certified that error appears in the above-identified patent and that said Letters Patent is hereby corrected as shown below:

In the Claims

In Column 27, Claim 10, Line 11, please delete "any preceding".

In Column 28, Claim 18, Lines 1-2, please delete "for illuminating".

Signed and Sealed this  
Sixth Day of February, 2018

Joseph Matal  
*Performing the Functions and Duties of the*  
*Under Secretary of Commerce for Intellectual Property and*  
*Director of the United States Patent and Trademark Office*